United States Patent
Grätzel et al.

(10) Patent No.: US 6,245,988 B1
(45) Date of Patent: Jun. 12, 2001

(54) METAL COMPLEX PHOTOSENSITIZER AND PHOTOVOLTAIC CELL

(75) Inventors: Michael Grätzel, Saint-Sulpice; Mohammad Khaja Nazeeruddin, Ecublens; Péter Péchy, Lausanne, all of (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/423,162

(22) PCT Filed: May 7, 1998

(86) PCT No.: PCT/IB98/00680

§ 371 Date: Nov. 2, 1999

§ 102(e) Date: Nov. 2, 1999

(87) PCT Pub. No.: WO98/50393

PCT Pub. Date: Nov. 12, 1998

(30) Foreign Application Priority Data

Jul. 5, 1997 (WO) .................... PCT/IB97/00518

(51) Int. Cl.⁷ .................... C07F 15/00; C07F 13/00; C07F 15/02; C09B 57/10; H01G 9/20

(52) U.S. Cl. .................... 136/263; 136/252; 257/40; 257/428; 257/431; 546/2; 546/10; 546/11; 546/12; 546/8; 546/9; 548/101; 548/107; 548/108; 548/109; 556/137; 556/138; 556/140; 556/145; 556/146; 534/14; 429/111

(58) Field of Search .................... 136/252, 263; 257/40, 428, 431; 546/2, 10, 11, 12, 8, 9; 548/101, 107, 108, 109; 534/14; 429/111; 556/137, 138, 140, 145, 146

(56) References Cited

U.S. PATENT DOCUMENTS 6,043,428 * 3/2000 Han et al. .................... 136/263

FOREIGN PATENT DOCUMENTS

WO 94/04497 * 3/1994 (WO) .
WO 95/29924 * 11/1995 (WO) .

OTHER PUBLICATIONS

Frank et al, "Photochemical Solar Cells Based on Dye-Sensitization of Nanocrystalline TiO2," American Institute of Physics, 1997.*
Pechy et al, J. Chem. Soc., Chem. Commun., 1995, pp. 65–66 (month unknown).*
Zakeeruddin et al, Inorg. Chem., 36(25), pp. 5937–5946, Dec. 1997.*
Chemical Abstract No. 128:130226a, Mar. 1998.*

* cited by examiner

*Primary Examiner*—Alan Diamond
(74) *Attorney, Agent, or Firm*—Cliford W. Browning; Woodard, Emhardt, Naughton Moriarty & McNett

(57) ABSTRACT

A photosensitizer complex of formulae (Ia) $MX_3L_t$ or (Ib) $MXYL_t$ in which M is a transition metal selected from ruthenium, osmium, iron, rhenium and technetium, preferably ruthenium or osmium; each X is a co-ligand independently selected from NCS—, Cl—, Br—, I—, CN—, NCO—, $H_2O$, $NCN^{2-}$; pyridine unsubstituted or substituted by at least one group selected from vinyl, primary, secondary or tertiary amine, OH and $C_{1-30}$ alkyl, preferably NCS—; and $L_t$ is a tridentate ligand comprising heterocycles such as pyridine, thiophene, imidazole, pyrazole, triazole, carrying at least one carboxylic, phosphoric, hydoxamic acid or a chelating group. A photovoltaic cell comprising an electrically conductive layer deposited on a support to which at least one titanium dioxide layer has been applied and, as a photosensitizer applied to the titanium dioxide layer, a photosensitizer complex of formula (Ia) or Ib) as specified above.

14 Claims, 3 Drawing Sheets

METAL COMPLEX PHOTOSENSITIZER AND PHOTOVOLTAIC CELL

The invention relates to a transition metal complex photosensitizer and its use in a photovoltaic cell comprising a nanocrystalline titanium dioxide layer.

Transition metal complexes, commonly designated as "dyestuffs", useful as charge transfer photosensitizer for semiconductive titanium dioxide photoanode layers, in a photovoltaic cell, are already known. Such complexes consist of a light absorber and an anchoring group. The anchoring group allows the immobilization of the transition metal complex at the titanium dioxide layers and provides an electronic coupling between the light absorber and the titanium dioxide layers. The light absorber absorbs an incoming photon via a metal ligand charge transfer, and injects an electron into the conduction band of titanium dioxide through the anchoring group. The oxidized complex is then regenerated by a redox mediator.

In such a process, it is crucial to guide the charge transfer toward the semiconductor titanium dioxide surface and to guarantee tight electronic overlap between the LUMO anchoring group and the vacant orbitals of titanium.

In particular, such complexes, as well as dye sensitized nanocrystalline titanium dioxide photovoltaic cells, are disclosed in the International Patent Applications published as PCT Publication No. WO 94/04497 and PCT Publication No WO 95/29924.

PCT Publication No. WO 94/04497 describes ruthenium complexes in which ruthenium is surrounded by at least one dicarboxy bipyridine ligand, the carboxy groups playing the role of anchoring groups. The best performing charge transfer photosensitizer employed for this application is cis-dithiocyanatobis(4,4'-dicarboxy-2,2'-bipyridine) ruthenium (II) complex. Using this complex in a nanocrystalline titanium dioxide photovoltaic cell has permitted to obtain a solar to electrical power conversion efficiency of 10% under standard spectral distribution of solar light emission AM 1.5, where the photosensitizer absorbs in the wavelength region from 400 to 650 nm. However, it has been found that in longer wavelength the incident photon to current conversion efficiency (IPCE) drops because of lack of spectral response of the photosensitizer.

PCT Publication No. WO 94/04497 describes other potent ruthenium complexes, being able to be immobilized at the titanium dioxide layers via at least one phosphonated group carried by polypyridine ligands. This particular anchoring group appeared to have a higher stability than the carboxy group on a wider pH range of 0 to 9, avoiding partial desorbtion of the complex. Unfortunately, the absorption spectrum upper limits of such complexes showed to be less than 600 nm.

The present invention aims at further improving the efficiency of solar to electric power conversion by providing a photosensitizer having an enhanced spectral response in the red and near infrared regions.

To that effect, according to the invention, there is provided a photosensitizer complex of formulae (Ia) or (Ib):

$MX_3L_t$ (Ia);

$MXYL_t$ (Ib);

M is a transition metal selected from ruthenium, osmium, iron, rhenium and technetium;

each X is a co-ligand independently selected from $NCS^-$, $Cl^-$, $Br^-$, $I^-$, $CN^-$, $NCO^-$, $H_2O$, $NCH^{2-}$ and pyridine unsubstituted or substituted by at least one group selected from vinyl, primary, secondary or tertiary amine, OH and $C_{1-30}$ alkyl;

Y is a co-ligand selected from o-phenanthroline, 2,2'-bipyridine, unsubstituted or substituted by at least one $C_{1-30}$ alkyl; and $L_t$ is a tridentate ligand having a formula selected from the general formulae (IIa) and (IIb):

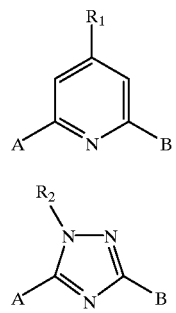

wherein $R_1$ is selected from H, COOH, $PO(OH)_2$, $PO(OR_3)_2$, CO(NHOH), pyrocatechol group and phenyl substituted by at least one of the groups selected from COOH, $PO(OH)_2$, $PO(OR_3)(OH)$, $PO(OR_3)_2$ and CO(NHOH); $R_3$ being selected from $C_{1-30}$ alkyl and phenyl;

$R_2$ is selected from H, $C_{1-30}$ alkyl and phenyl; and

A and B are same or different groups independently selected from the groups of formulae (IIIa), (IIIb), (IIIc), (IIId), (IIIe) and (IIIf):

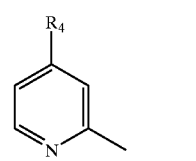

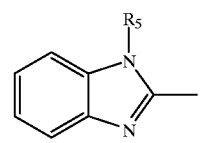

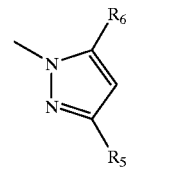

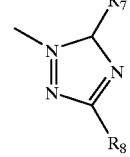

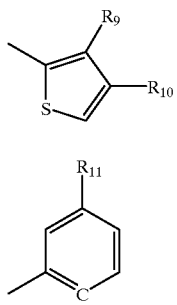

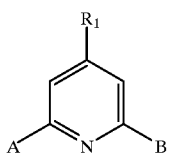

wherein
$R_4$ has the same meaning as $R_1$;
each $R_5$, $R_6$, $R_7$, $R_8$, $R_9$, $R_{10}$ and $R_{11}$ has the same meaning as $R_2$ and $R_2$, $R_5$, $R_6$, $R_7$, $R_8$, $R_9$, $R_{10}$ and $R_{11}$ being same as or different from each other;
with the proviso that at least one of the substituents $R_1$ and $R_4$ is different of H.

More preferably, when the photosensitizer complex corresponds to formula (Ia):

$$MX_3L_t \qquad (Ia),$$

M is ruthenium or osmium;
each X is independently selected from $NCS^-$, $CN^-$, and $L_t$ has the formula (IIa):

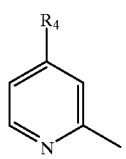

wherein
$R_1$ is selected from H, COOH, $PO(OH)_2$, $PO(OR_3)(OH)$, $PO(OR_3)_2$, CO(NHOH), pyrocatechol group and phenyl substituted by at least one of the groups selected from COOH, $PO(OH)_2$, $PO(OR_3)_2$ and CO(NHOH); $R_3$ being selected from $C_{1-30}$ alkyl and phenyl;
A and B are same or different and have the formula (IIIa):

wherein
$R_4$ has the same meaning as $R_1$;
with the proviso that at least one of the substituents $R_1$ and $R_4$ is different of H.

More preferably, when the photosensitizer complex corresponds to formula (Ia):

$$MX_3L_t \qquad (Ia),$$

M is ruthenium or osmium;
each X is independently selected from $NCS^-$, $CN^-$, and $L_t$ has the formula (IIa):

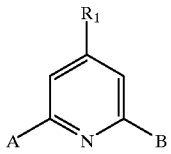

wherein
$R_1$ is a phenyl substituted by at least one of the groups selected from COOH, $PO(OH)_2$, $PO(OR_3)(OH)$, $PO(OR_3)_2$; $R_3$ being selected from $C_{1-30}$ alkyl and phenyl; and
A and B are both 2-pyridyl.

More preferably, when the photosensitizer complex corresponds to formula (Ia):

$$MX_3L_t \qquad (Ia),$$

M is ruthenium or osmium;
each X is independently selected from $NCS^-$, $CN^-$, and $L_t$ has the formula (IIa):

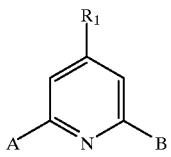

wherein
$R_1$ is COOH; and
A and B are both 4-carboxy-2-pyridyl.

Preferably, when the photosensitizer complex corresponds to formula (IIb):

$$MXYL_t \qquad (Ib),$$

M is ruthenium or osmium;
X is $NCS^-$, $CN^-$;
Y is selected from o-phenanthroline, 2,2'-bipyridine, unsubstituted or substituted by at least one $C_{1-30}$ alkyl; and
$L_t$ has the formula (IIa):

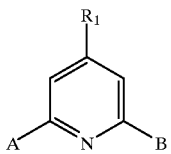

wherein
$R_1$ is selected from H, pyrocatechol group, phenyl substituted by at least one of the groups selected from COOH, $PO(OH)_2$, $PO(OR_3)(OH)$, $PO(OR_3)_2$ and CO(NHOH);
$R_3$ being selected from $C_{1-30}$ alkyl and phenyl;

A and B are same or different and have the formula (IIIa):

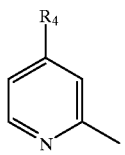

IIIa wherein $R_4$ is selected from H, COOH, $PO(OH)_2$, $PO(OR_3)(OH)$, $PO(OR_3)_2$, CO(NHOH), pyrocatechol group, phenyl substituted by at least one of the groups selected from COOH, $PO(OH)_2$, $PO(OR_3)(OH)$, $PO(OR_3)_2$ and CO(NHOH); $R_3$ being selected from $C_{1-30}$ alkyl and phenyl;

with the proviso that at least one of the substituents $R_1$ and $R_4$ is different of H.

More preferably, when the photosensitizer complex corresponds to formula (Ib):

$MXYL_t$ (Ib),

M is ruthenium or osmium;
Y is 4,4'-dimethyl-2,2'-bipyridine; and
$L_t$ has the formula (IIa):

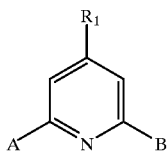

IIa wherein $R_1$ is a phenyl substituted by at least one of the groups selected from COOH, $PO(OH)_2$, $PO(OR_3)(OH)$ and $PO(OR_3)_2$; $R_3$ being selected from $C_{1-30}$ alkyl and phenyl; and A and B are both 2-pyridyl.

The invention results from extensive research which have shown that the transition metal complex of formulae (Ia) and (Ib) has the unexpected property of exhibiting a substantially enhanced spectral response in the red and near infrared regions, in comparison with the prior art transition metal complexes.

This property allows the use of the complex of formulae (Ia) or (Ib) as charge transfer photosensitizer for semiconductive titanium dioxide photoanode layers, in a photovoltaic cell with a very efficient panchromatic sensitization over the whole visible radiation spectrum, extending into the near infrared region up to 920 nm.

It appeared that the type of coordination around the transition metal, in particular ruthenium or osmium, and the nature of the ligand $L_t$ and the co-ligands Y and/or X surrounding the metal are crucial for obtaining such spectral properties and the claimed combination of ligand and co-ligands has a favourable match to the solar spectrum for efficient energy conversion. This is particularly the case when the co-ligands X are the negatively charged species such as the cyanide anion or the thiocyanide anion and when the co-ligand Y is the electron-donor 4,4'-dimethyl-2,2'-bipyridine.

Among the potent tridentate ligands $L_t$, offering furthermore to the photosensitizer complex at least one anchoring group selected from carboxylate group [COOH], phosphonate group [$PO(OH)_2$, $PO(OR_3)(OH)$ or $PO(OR_3)_2$], hydroxamate group [CO(NHOH)] or chelating groups such as salicylate group [o-carboxyhydroxy-phenyl] or pyrocatechol group [o-dihydroxy-phenyl], the compounds having the following formulae contribute for the best to the increase of spectral properties of the photosensitizer:

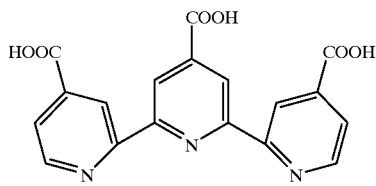

(1)

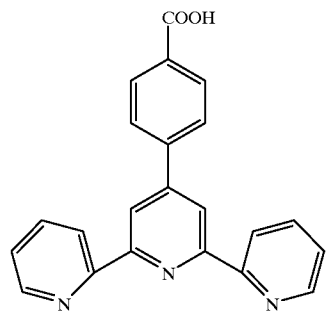

(2)

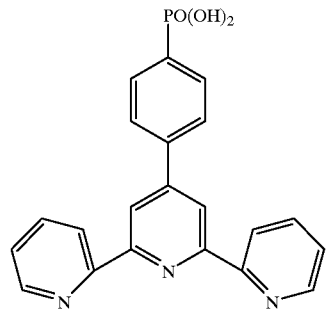

(3)

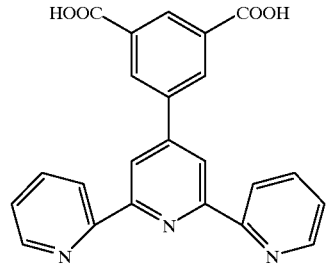

(4)

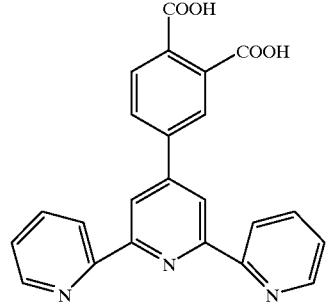

(5)

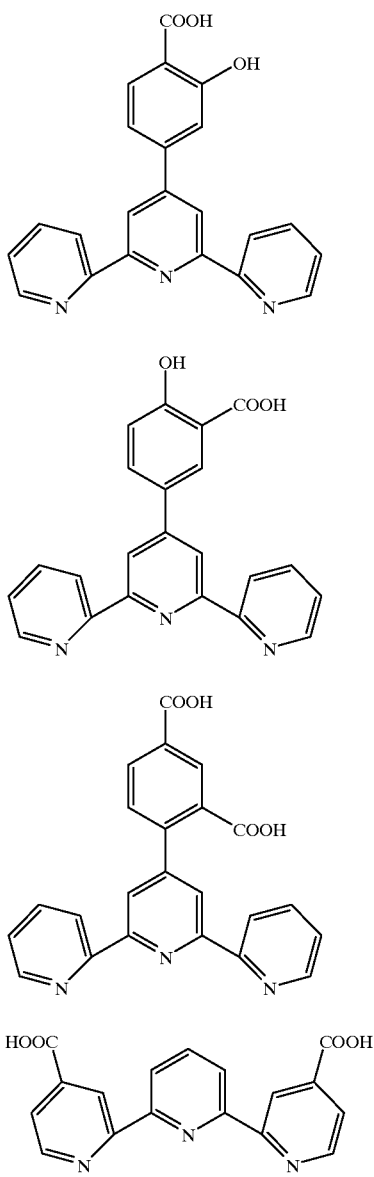

Still further according to the invention, there is provided a photovoltaic cell comprising an electrically conductive layer deposited on a support to which at least one titanium dioxide layer has been applied, characterized in that it comprises, as a photosensitizer applied to the titanium dioxide layer, a photosensitizer complex of formulae (Ia) or (Ib) as specified above.

BRIEF DESCRIPTION OF THE DRAWINGS

The invention will now be illustrated by the following examples, with reference to the attached drawing, in which.

EXAMPLE 1

Figure 1:
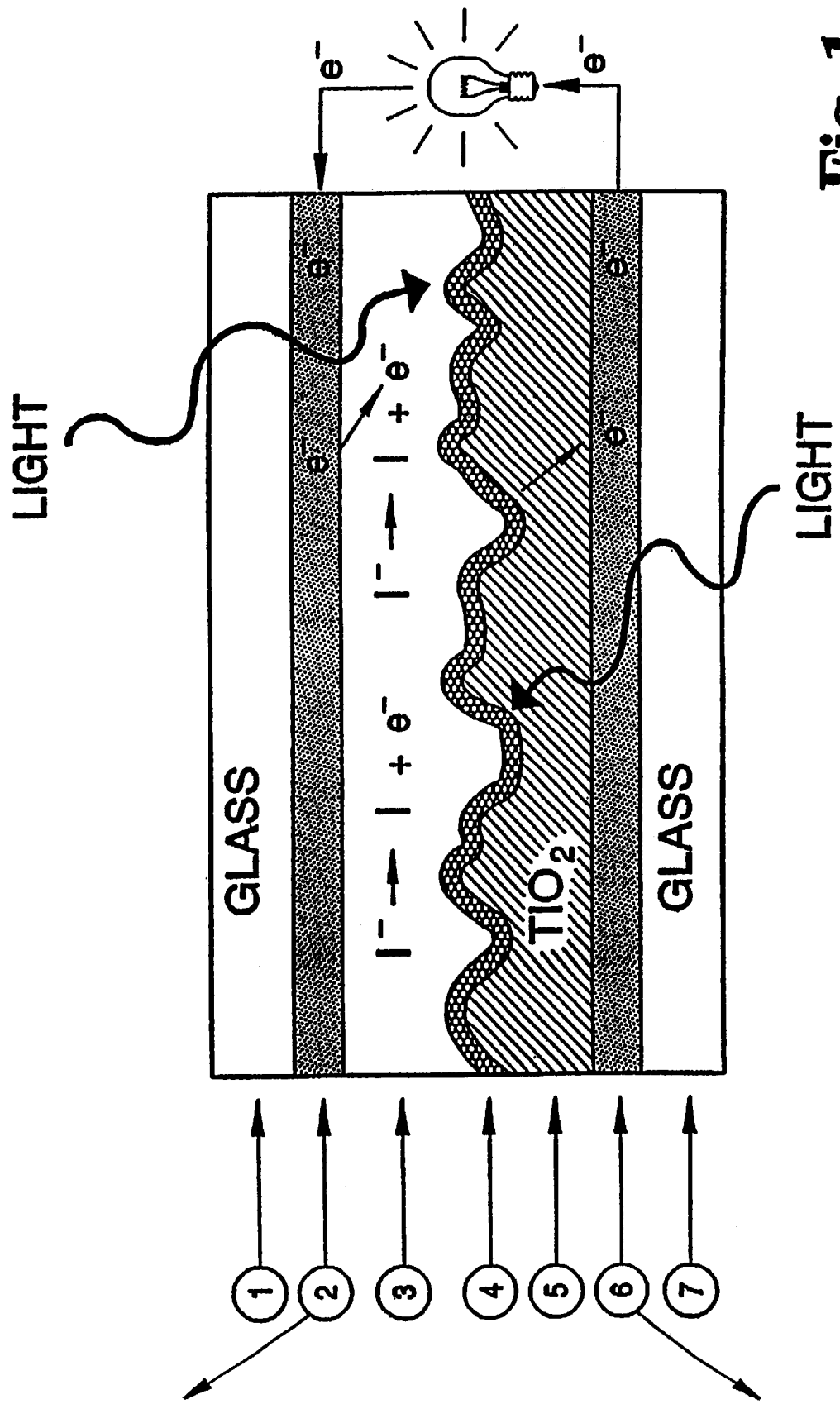
FIG. 1 is a schematic illustration of the layout and function of a photovoltaic cell comprising a photoanode provided with a nanostructured semiconductive titanium dioxide film having a transition metal complex of formulae (Ia) or (Ib) applied thereto as a charge transfer sensitizer.

Preparation of the complex trithiocyanato (4,4',4''-tricarboxy-2,2':6',2''-terpyridyl) ruthenium(II), i.e. the complex of formula $Ru(NCS)_3L_t$, wherein $L_t$ is 4,4',4''-tricarboxy-2,2':6',2''-terpyridine a) Preparation of 4,4',4''-trimethyl-2,2':6',2''-terpyridine:

4-Methyl-pyridine (900 mL, refluxed over and distilled fresh from KOH pellets) and palladium on charcoal (5%, 37 g) were heated on a bath at 170° C. as long as the chemical equilibrium is reached. The reaction mixture was filtered hot, the catalyst was washed with hot toluene and the filtrate left to crystallise. The 4,4'-dimethyl- 2,2'-bipyridine crystals were filtered and washed with toluene. The mother liquors combined, concentrated to ⅓ of the volume and crystallised at 0° C. This second crop of bipyridine was treated as above, the mother liquor was evaporated to dryness under reduced pressure. The bipyridine and terpyridine components of the mother liquor were separated by careful multiple fractional sublimations at 0.02 mmHg, at bath temperatures 80–100° C. (depending on the geometry of the apparatus). Under these conditions, the 4,4',4''-trimethyl-2,2':6',2''-terpyridine accumulates in the residue. The combined pure terpyridine fractions were sublimed twice at 0.02 mmHg at 120–140° C. yielding 15 g of off-white 4,4',4''-trimethyl-2,2':6',2''-terpyridine. (For some fractions column chromatography on silicagel with dichloromethane as eluent was used to get the highly pure 4,4',4''-trimethyl-2,2':6',2''-terpyridine.)

MS (70 eV, chem.ionisation/NH3) m/e (rel.int.): 277(6.6, M+2), 276 (37.8; M+1), 275 (100.0; M), 274 (25.8), 260 (3.91, M-15), 247 (1.4, M-28), 233 (1.9, M-42), 183 (1.1, M-92), 92(4.58, M-183).

$^1$H-NMR (CDCl$_3$) δ ppm: 2.50 (6H, s), 2.58 (3H, s), 7.15 (2H, d), 8.26 (2H, s), 8.40 (2H, s), 8.55 (2H, d).

b) Preparation of 4,4'4''-tricarboxy-2,2';6',2''-terpyridine;

To an ice-cold solution of 4,4',4''-trimethyl-2,2';6',2''-terpyridine (0.32 g; 1.16 mmol) in sulfuric acid (4 mL) chromium trioxide (1.05 g; 10.5 mmol) was added. Stirred for 4 h at 75° C., poured to 50 ml ice-water, then diluted with water (165 ml) and the white precipitate was separated within a centrifuge, washed until pH=7, and dried. Yielding 4,4',4''-tricarboxy-2,2';6',2''-terpyridine (0.15 g; 41%) as a greenish white amorphous powder.

MS (70 eV, chem.ionisation/NH3) m/e (rel.int.): 366 (12.22, M+1), 365 (12.57; M), 322 (16.44), 321 (55.11, M-44), 293 (4.05), 231 (1.34, M-3×44+3), 79 (100).

$^1$H-NMR (D$_2$O/NaOH) δ ppm: 7.52 (2H, d), 8.13 (2H, s), 8.31 (2H, s), 8.43 (2H, d) 8.40 (2H, s), 8.55 (2H, d).

c) Preparation of the tetrabutylammonium salt of trithiocyanato (4,4',4''-tricarboxy-2,2':6',2''-terpyridyl) ruthenium (II):

RuCl$_3$.xH2O (60 mg, 0.23 mmol) and 4,4',4''-tricarboxy-2,2':6'2''-terpyridine (70 mg, 0.19 mmol) were added to a 100 mL three necked flask containing 30 mL of DMF and nitrogen bubbled through the mixture for 15 minutes. The mixture was protected from light by wrapping aluminium foil around the flask and then heated at 120° C. for two hours. The brown-green solution was cooled slightly, 110° C., and excess KSCN (0.9 g, 9 mmol) dissolved in 5 mL of a 4:1 mixture of DMF/water added and heating continued for a further 70 hours at the same temperature under exclusion of light. The colour of the mixture changed for brown-green to green after this time. Base in the form of solid hydrated tetrabutylammonium hydroxide (TBAOH, 0.48 g) was then added and the mixture heated at 110° C. for a further 24 hours. The reaction mixture was reduced to almost dryness on a rotary evaporator and a further 0.6 g of TBAOH added followed by ca. 100 mL of deionised water (the pH of the solution was ca. 11.7). The resulting purple solution was filtered to remove a small amount of insoluble material and the pH adjusted to 4 with dilute hydrochloric acid. A dark green precipitate formed immediately but the suspension was nevertheless refrigerated overnight prior to filtration to collect the product. Yield: 192 mg (87%) of the tetrabutylammonium salt of trithiocyanato (4,4',4"-tricarboxy-2,2':6',2"-terpyridyl) ruthenium(II). Gel-permeation chromatography can be used to further purify the product.

Microanalyses: Found: C, 54.7; H, 7.0, N, 10.1. Calcd for $C_{53}H_{81}N_8O_6S_3Ru.2H_2O$: C, 54.9; H, 7.4, N 9.7

The UV-VIS absorption spectrum of the complex in ethanol shows an intense metal-to-ligand charge transfer band at 620 nm.

$^1$H-NMR Spectrum (CD$_3$OD, ppm): 1.03 (t, 24H, CH$_3$), 1.55 (q, 16H, CH$_2$CH$_3$), 1.70 (m, 16H, NCH$_2$CH$_2$), 3.28 (t, 16H, NCH$_2$), 8.23 (dd, 2H, H-5, H-5') 8.95 (d, 2H, H-3, H-3'; s, 2H, H-3"), 9.17 (d, 2H, H-6, H-6").

$^{13}$C NMR Spectrum (CD$_3$OD, ppm); 13.95, 20.74, 24.83, 59.6, 122,12, 122.99, 129.89, 136.62, 138.16, 142.30, 154.86, 160.80, 162.19, 167.66.

EXAMPLE 2

Preparation of the complex trithiocyanato (4'-(4-phenylphosphonate)-2,2':6',2"-terpyridyl) ruthenium(II), i.e. the complex of formula Ru(NCS)$_3$L$_t$, wherein L$_t$ is 4'-(4-phenylphosphonate)-2,2':6',2"-terpyridine a) Preparation of 4'-(4-phenylphosphonate)-2,2';6',2"-terpyridine:

This ligand was prepared following a described procedure (H. Toshikazu et al., Syntheses, 1961, 56)

b) Preparation of the tetrabutylammonium salt of trithiocyanato (4'-(4-phenylphosphonate)-2,2',6',2"-terpyridyl) ruthenium(II):

This complex was prepared by an analogous procedure to that described in Example 1.

The UV-VIS absorption spectrum of the complex in ethanol shows an intense metal-to-ligand charge transfer band at 580 nm.

EXAMPLE 3

Preparation of the complex trithiocyanato (4'-(4-carboxyphenyl)-2,2':6',2"-terpyridyl) ruthenium(II), i.e. the complex of formula Ru(NCS)$_3$L$_t$, wherein L$_t$ is 4-(4-carboxyphenyl)-2,2':6',2"-terpyridine a) Preparation of 4'-(4-carboxyphenyl)-2,2';6',2"-terpyridine:

This ligand was prepared by oxidation of the known (4'-(4-methylphenyl)-2,2',6',2"-terpyridyl) by an analogous procedure to that described in Example 1b.

b) Preparation of the tetrabutylammonium salt of trithiocyanato (4'-(4-carboxyphenyl)-2,2',6',2"-terpyridyl) ruthenium(II):

This complexe was prepared by an analogous procedure to that described in Example 1.

The UV-VIS absorption spectrum of the complex in ethanol shows an intense metal-to-ligand charge transfer band at 600 nm.

EXAMPLE 4

Preparation of the complex tricyano (4,4',4"-tricarboxy-2,2':6',2"-terpyridyl) ruthenium(II), i.e. the complex of formula Ru(NC)$_3$L$_t$, wherein L$_t$ is 4,4',4"-tricarboxy-2,2':6',2"-terpyridine The tetrabutylammonium salt of this complexe was prepared by an analogous procedure to that described in Example 1.

The UV-VIS absorption spectrum of the complex in ethanol shows an intense metal-to-ligand charge transfer band at 540 nm.

EXAMPLE 5

Preparation of the complex tricyano (4'-(4-phenylphosphonate)-2,2':6',2"-terpyridyl) ruthenium(II), i.e. the complex of formula RU(NC)$_3$L$_t$, wherein L$_t$ is 4'-(4-phenylphosphonate)-2,2':6',2"-terpyridine The tetrabutylammonium salt of this complexe was prepared by an analogous procedure to that described in Example 1.

The UV-VIS absorption spectrum of the complex in ethanol shows an intense metal-to-ligand charge transfer band at 520 nm.

EXAMPLE 6

Preparation of the complex tricyano (4'-(4-carboxyphenyl)-2,2':6',2"-terpyridyl) ruthenium(II), i.e. the complex of formula Ru(NC)$_3$L$_t$, wherein L$_t$ is 4'-(4-carboxyphenyl)-2,2':6',2"-terpyridine The tetrabutylammonium salt of this complexe was prepared by an analogous procedure to that described in Example 1.

The UV-VIS absorption spectrum of the complex in ethanol shows an intense metal-to-ligand charge transfer band at 530 nm.

EXAMPLE 7

Preparation of the complex thiocyanato (4'-(4-phenylphosphonate)-2,2':6',2"-terpyridyl)(4,4'-dimethyl-2,2'-bipyridyl) ruthenium(II), i.e. the complex of formula Ru(NCS)YL$_t$, wherein L$_t$ is 4'-(4-phenylphosphonate-2,2':6',2"-terpyridine and Y is 4,4'-dimethyl-2,2'-bipyridine.

The synthesis and work-up of this reaction were performed under reduced light in order to avoid possible isomerization. RuCl$_3$(dmso)$_4$ (0.484 g) was dissolved into a 100 mL three necked flask containing 30 mL of DMF and nitrogen bubbled through the mixture for 15 minutes. To this solution was added (0.375 g) 4'-(4-phenyl-phosphonate)-2,2':6',2"-terpyridine. The reaction flask was protected from light by wrapping aluminum foil around the flask and then heated at 120° C. for three hours. To this solution was added 4,4'-dimethyl-2,2'-bipyridine ligand (0.184 g), and refluxed under a nitrogen atmosphere for another 4 hours. The reaction mixture was cooled to 110° C., and excess KSCN (0.9 g, 9 mmol) dissolved in 5 mL of a 4:1 mixture of DMF/water added and heating continued for a further 5 hours at the same temperature under exclusion of light. The colour of the mixture changed after this time. Base in the form of solid hydrated tetrabutylammonium hydroxide (TBAOH, 0.48 g) was then added and the mixture heated to 110° C. For a further 4 hours. The reaction mixture was reduced to almost dryness on a rotary evaporator and a further 0.6 g of TBAOH added followed by ca. 100 mL of deionised water (the pH of the solution was ca. 11.7). The resulting purple solution was filtered to remove a small amount of insoluble material and the pH adjusted to 2.5 with dilute hydrochloric acid. A dense precipitate formed immediately but the suspension was nevertheless refrigerated overnight prior to filtration to collect the product. After allowing it to cool to (25° C.) room temperature, it was filtered through a sintered (G-4) glass crucible and dried under vacuum. Yield 60% of the tetrabutylammonium salt of thiocyanato (4'-(4-phenylphosphonate)-2,2':6',2"-terpyridyl)(4,4'-dimethyl-2,2'-bipyridyl) ruthenium(II).

The UV-VIS absorption spectrum of this complex in ethanol shows an intense metal-to-ligand charge transfer band at 500 nm.

EXAMPLE 8

Preparation of the complex thiocyanato (4'-(4-carboxyphenyl-2,2':6',2"-terpyridyl)(4,4'-dimethyl-2,2'-bipyridyl) ruthenium(II), i.e. the complex of formula Ru(NCS)YL$_t$, wherein L$_t$ is 4'-(4-carboxyphenyl)-2,2':6',2"-terpyridine and Y is 4,4'-dimethyl-2,2'-bipyridine The tetrabutylammonium salt of this complexe was prepared by an analogous procedure to that described in Example 7.

The UV-VIS absorption spectrum of the complex in ethanol shows an intense metal-to-ligand charge transfer band at 510 nm.

EXAMPLE 9

Preparation of the complex thiocyanato (4,4',4"-tricarboxy-2,2':6',2"-terpyridyl)(4,4'-dimethyl-2,2'-bipyridyl) ruthenium(II), i.e. the complex of formula Ru(NCS)YL$_t$, wherein L$_t$ is 4,4'4"-tricarboxy-2,2':6',2"-terpyridine and Y is 4,4'-dimethyl-2,2'-bipyridine.

The tetrabutylammonium salt of this complexe was prepared by an analogous procedure to that described in Example 7.

The UV-VIS absorption spectrum of the complex in ethanol shows an intense metal-to-ligand charge transfer band at 520 nm.

EXAMPLE 10

Preparation of the complex cyano (4'-(4-phenylphosphonate)-2,2':6',2"-terpyridyl)(4,4'-dimethyl-2,2'-bipyridyl) ruthenium(II), i.e. the complex of formula Ru(NC)YL$_t$, wherein L$_t$ is 4'-(4-phenylphosphonate)-2,2':6',2"-terpyridine and Y is 4,4'-dimethyl-2,2'-bipyridine.

The tetrabutylammonium salt of this complexe was prepared by an analogous procedure to that described in Example 7.

The UV-VIS absorption spectrum of the complex in ethanol shows an intense metal-to-ligand charge transfer band at 500 nm.

EXAMPLE 11

Preparation of the complex cyano (4'-(4-carboxyphenyl-2,2':6',2"-terpyridyl)(4,4'-dimethyl-2,2'-bipyridyl) ruthenium(II), i.e. the complex of formula Ru(NC)YL$_t$, wherein L$_t$ is 4'-(4-carboxyphenyl)-2,2':6',2"-terpyridine and Y is 4,4'-dimethyl-2,2'-bipyridine.

The tetrabutylammonium salt of this complexe was prepared by an analogous procedure to that described in Example 7.

The UV-VIS absorption spectrum of the complex in ethanol shows an intense metal-to-ligand charge transfer band at 510 nm.

EXAMPLE 12

Preparation of the complex cyano (4,4',4"-tricarboxy-2,2':6',2"-terpyridyl)(4,4'-dimethyl-2,2'-bipyridyl) ruthenium(II), i.e. the complex of formula Ru(NC)YL$_t$, wherein L$_t$ is 4,4',4"-tricarboxy-2,2':6',2"-terpyridine and Y is 4,4'-dimethyl-2,2'-bipyridine.

The tetrabutylammonium salt of this complexe was prepared by an analogous procedure to that described in Example 7.

The UV-VIS absorption spectrum of the complex in ethanol shows an intense metal-to-ligand charge transfer band at 520 nm.

EXAMPLE 13

Preparation of the complex cyano (4'-(4-carboxyphenyl)-2,2':6',2"-terpyridyl)(4,4'-dimethyl-2,2'-bipyridyl) osmium(II), i.e. the complex of formula Os(NC)YL$_t$, wherein L$_t$ is 4'-(4'-carboxyphenyl)-2,2':6',2"-terpyridine and Y is 4,4'-dimethyl-2,2'-bipyridine.

The tetrabutylammonium salt of this complexe was prepared by an analogous procedure to that described in Example 7 using NH$_4$OsCsCl$_6$ and ethyleneglycol as solvent.

The UV-VIS absorption spectrum of the complex in ethanol shows an intense metal-to-ligand charge transfer band at 510 nm, 650 nm and 700 nm.

EXAMPLE 14

Preparation of the complex cyano (4,4',4"-tricarboxy-2,2':6',2"-terpyridyl)(4,4'-dimethyl-2,2'-bipyridyl) osmium(II), i.e. the complex of formula Os(NC)YL$_t$, wherein L$_t$ is 4,4',4"-tricarboxy-2,2':6',2"-terpyridine and Y is 4,4'-dimethyl-2,2'-bipyridine.

The tetrabutylammonium salt of this complexe was prepared by an analogous procedure to that described in Example 13.

The UV-VIS absorption spectrum of the complex in ethanol shows an intense metal-to-ligand charge transfer band at 510 nm, 650 nm and 700 nm.

EXAMPLE 15

Preparation of the complex cyano (4'(4-phenylphosphonate)-2,2':6',2"-terpyridyl)(4,4'-dimethyl-2,2'-bipyridyl) osmium(II), i.e. the complex of formula Os(NC)YL$_t$, wherein L$_t$ is 4'-(4-phenylphosphonate)-2,2':6',2"-terpyridine and Y is 4,4'-dimethyl-2,2'-bipyridine.

The tetrabutylammonium salt of this complexe was prepared by an analogous procedure to that described in Example 13.

The UV-VIS absorption spectrum of the complex in ethanol shows an intense metal-to-ligand charge transfer band at 400 nm, 640 nm, and 700 nm.

EXAMPLE 16

Preparation of the complex thiocyanato (4'-(4-phenylphosphonate)-2,2':6',2"-terpyridyl)(4,4'-dimethyl-2, 2'-bipyridyl) osmium(II), i.e. the complex of formula Os(NC)YL$_t$, wherein L$_t$ is 4'-(4-phenylphosphonate)-2,2':6', 2"-terpyridine and Y is 4,4'-dimethyl-2,2'-bipyridine.

The tetrabutylammonium salt of this complexe was prepared by an analogous procedure to that described in Example 13.

The UV-VIS absorption spectrum of the complex in ethanol shows an intense metal-to-ligand charge transfer band at 510 nm, 650 nm and 700 nm.

Application Example

A photovoltaic device shown in FIG. 1 and based on the sensitization of a titanium dioxide film supported on conducting glass is fabricated as follows:

Nanocrystalline TiO$_2$ films were prepared by spreading a viscous dispersion of colloidal TiO$_2$ particles on a conducting glass support (Asahi TCO glass, fluorine-doped SnO$_2$ overlayer, transmission>85% in the visible sheet resistance 7–8 Ω/square) with heating under air for 30 min at 450° C. Two methods of preparation of colloid TiO$_2$ dispersions were employed. Method A followed the procedure described earlier [O'Regan, B.; Grätzel, M. *Nature* (London) 1991, 353, 737], except that autoclaving was performed at 230 or 240° C. instead of 200° C. After the colloid was spread on the conducting glass support and calcined, a few monolayers of TiO$_2$ were electrodeposited [Kavan, L.; O'Regan, B.; Kay, A.; Grätzel, M. *J. Electroanal. Chem.* 1993, 346, 291] onto the colloid TiO$_2$ film from an aqueous Ti(III) solution followed by renewed annealing at 450° C. This treatment was found to improve significantly the short-circuit photocurrent as well as the open-circuit voltage of the solar cell. A cross section of such a TiO$_2$ film obtained by scanning electron microscopy at two different magnifications confirms the presence of a three-layer structure, the lowest being the glass support followed by the 0,7-μm-thick fluorine-doped SnO$_2$ and the 10-μm-thick colloidal TiO$_2$ film. High resolution reveals the TiO$_2$ film to be composed of a three-dimensional network of interconnected particles having an average size of approximately 15 nm.

The second method for preparation of nanocrystalline films (Method B) employed commercial TiO$_2$ (P25, Degussa AG, Germany, a mixture of ca. 30% rutile and 70% anatase, BET surface area 55 m$^2$/g). This is produced by flame hydrolysis of TiCl$_4$ and consists of aggregated particles. Electron microscopy shows the mean size of primary particles to be about 25 nm. In order to break the aggregates into separate particles, the powder (12 g) was ground in a porcelain mortar with a small amount of water (4 mL) containing acetylacetone (0,4 mL) to prevent reaggregation of the particles. Other stabilizers such as acids, bases, or TiO$_2$ chelating agents were found to be suitable as well. After the powder had been dispersed by the high shear forces in the viscous paste, it was diluted by slow addition of water (16 mL) under continued grinding. Finally, a detergent (0,2 mL Triton X-100, Aldrich) was added to facilitate the spreading of the colloid on the substrate. The conducting TCO glass was covered on two parallel edges with adhesive tape (≈40-μm-thick) to control the thickness of the TiO$_2$ film and to provide noncoated areas for electrical contact. The colloid (5 μL/cm$^2$) was applied to one of the free edges of the conducting glass and distributed with a glass rod sliding over the tape-covered edges. After air drying, the electrode was fired for 30 min at 450–550° C. in air. The resulting film thickness was 12 μm but can be varied by changing the colloid concentration or the adhesive tape thickness.

The performance of the film as a sensitized photoanode was improved by further deposition of TiO$_2$ from aqueous TiCl$_4$ solution. A 2M TiCl$_4$ stock solution was prepared [Kavan, L.; O'Regan, B.; Kay, A.; Grätzel, M. *J. Electroanal. Chem.* 1993, 346, 291] at 0° C. to prevent precipitation of TiO$_2$ due to the highly exothermic hydrolysis reaction. This stock solution was freshly diluted with water to 0.2 M TiCl$_4$ and applied onto the electrode (50 μL/cm$^2$). After being left overnight at room temperature in a closed chamber, the electrode was washed with distilled water. Immediately before being dipped into the dye solution, it was fired again for 30 min at 450–550° C. in air. Similarly to the electrodeposition from aqueous Ti(III) solution, this procedure results in the nucleation of nanometer-sized TiO$_2$ particles on the TiO$_2$ film, further increasing its active surface area. Furthermore, this treatment as well as the anodic deposition of TiO$_2$ from Ti(III) solution described above appears to lead to deposits having a very low impurity content. This is corroborated by the fact that the treatment becomes ineffective if the TCl$_4$ solution is evaporated before firing instead of being washed off. Impurities in the TiCl$_4$, such as Fe$^{3+}$, are not deposited by hydrolysis from the acidic TiCl$_4$ solution due to the higher solubility of iron oxide compared to TiO$_2$. By contrast, evaporation of the TiCl$_4$ solution results in the deposition of impurities. The P25 powder contains up to 100 ppm of Fe$_2$O$_3$, which is known to interfere with electron injection from the excited dye. The TiCl$_4$ treatment covers this rather impure core with a thin layer of highly pure TiO$_2$, improving the injection efficiency and the blocking character of the semiconductor electrolyte junction [Kavan, L.; O'Regan, B.; Kay, A.; Grätzel, M. *J. Electroanal. Chem.* 1993, 346, 291].

The above described treatment produces anatase films with a surface roughness factor of about 200 to 1000.

After cooling under a continuous argon flow the glass sheet is immediately transferred to a 2×10$^{-4}$M solution in ethanol of the tetrabutylammonium salt of the ruthenium complex of Example 1, this solution further containing 40 mM of tauro-deoxycholic acid as a co-adsorbent. Prolonged exposure of the film to the open air prior to dye adsorption is avoided in order to prevent hydroxylation of the TiO$_2$ surface as the presence of hydroxyl groups at the electrode surface interferes with dye uptake. The adsorption of photosensitizer from the ethanolic solution is allowed to continue for 10 hours after which time the glass sheet is withdrawn and washed briefly with absolute ethanol. The TiO$_2$ layer on the sheet assumed a black colour owing to the photosensitive coating.

Figure 2:
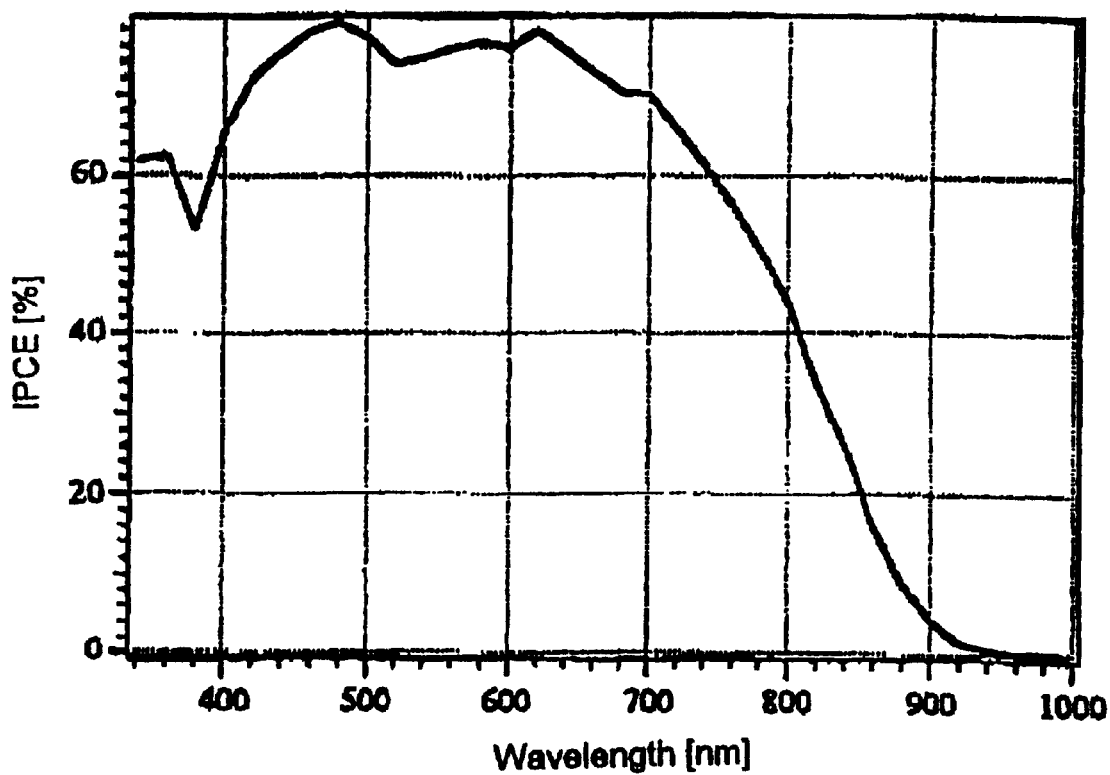
FIG. 2 is a graph showing the photocurrent action spectrum of such a cell where the incident photon to current conversion efficiency (IPCE) is plotted as a function of wavelength.

A thus obtained black colored film, having a thickness of 12 mm, exhibited striking performance when tested in a photovoltaic cell in conjunction with a redox electrolyte containing a solution of 60% methoxypropionitrile, 40% acetonitrile, 0.5M 4-tert-butylpyridine, 0.1M LiI, 0.6M 1,2-dimethyl-3-propyl imidazoliumiodide and 0.1M I$_2$. FIG. 2 shows the photocurrent action spectrum of such a cell where the incident photon to current conversion efficiency (IPCE) is plotted as a function of the excitation wavelength. This was derived from the equation:

$$IPCE(\%) = \frac{[(1.24 \times 10^3) \times \text{photocurrent density } (\mu A/cm^2)]}{[\text{wavelength (nm)} \times \text{photon flux } (W/m^2)]} \quad (1)$$

From the overlap of the photocurrent action spectrum with solar emission the overall efficiency for the conversion of solar light to electricity η is calculated from the formula $$\eta = 12 \times OCV \times FF(\%) \quad (2)$$

where OCV is the open circuit voltage and FF is the fill factor of the photovoltaic cell.

For experimental verification of equation 2, a photovoltaic cell, as illustrated on FIG. 1, is constructed, using the ruthenium complex of Example 1 (4) by way of photosensitizer loaded TiO$_2$ (5) film supported on a conducting glass (the working electrode) comprising a transparent conductive tin dioxide layer (6) and a glass substrate (7) as a photoanode. The cell has a sandwich-like configuration, the working electrode (4–7) being separated from the counter electrode (1,2) by a thin layer of electrolyte (3) having a thickness of ca. 20 microns. The counter-electrode comprises the conductive tin dioxide layer (2) deposited on a glass substrate (1) made also of Asahi conducting glass and is placed directly on top of the working electrode. A monomolecular transparent layer of platinum is deposited on to the conducting glass of the counter electrode (1,2) by electroplating from an aqueous hexachloroplatinate solution. The role of the platinum is to enhance the electrochemical reduction of iodine at the counter electrode. The transparent nature of the counterelectrode is an advantage for photovoltaic applications since it allows the harvesting of light from both the forward and the backward direction. Experiments are carried out with a high pressure Xenon lamp equipped with appropriate filters to simulate AM1,5 solar radiation. The intensity of the light is varied between 50 and 600 Watts per square meter and the open circuit voltage is 660 and 800 mV, respectively. The fill factor defined as the maximum electric power output of the cell divided by the product of open circuit voltage and short circuit current is between 0.7 and 0.75 V. The broad feature covering the entire visible spectrum and extending into the near IR region up to 920 nm is obtained, the IPCE value in the plateau region being about 80%. Taking the light losses in the conducting glass into account the efficiency of electric current generation is practically 100% over a broad wavelength range extending from 400 to 700 nm. The overlap integral of this curve with the standard global AM 1.5 solar emission spectrum yields a photocurrent density of 20 m A/cm$^2$.

Figure 3:
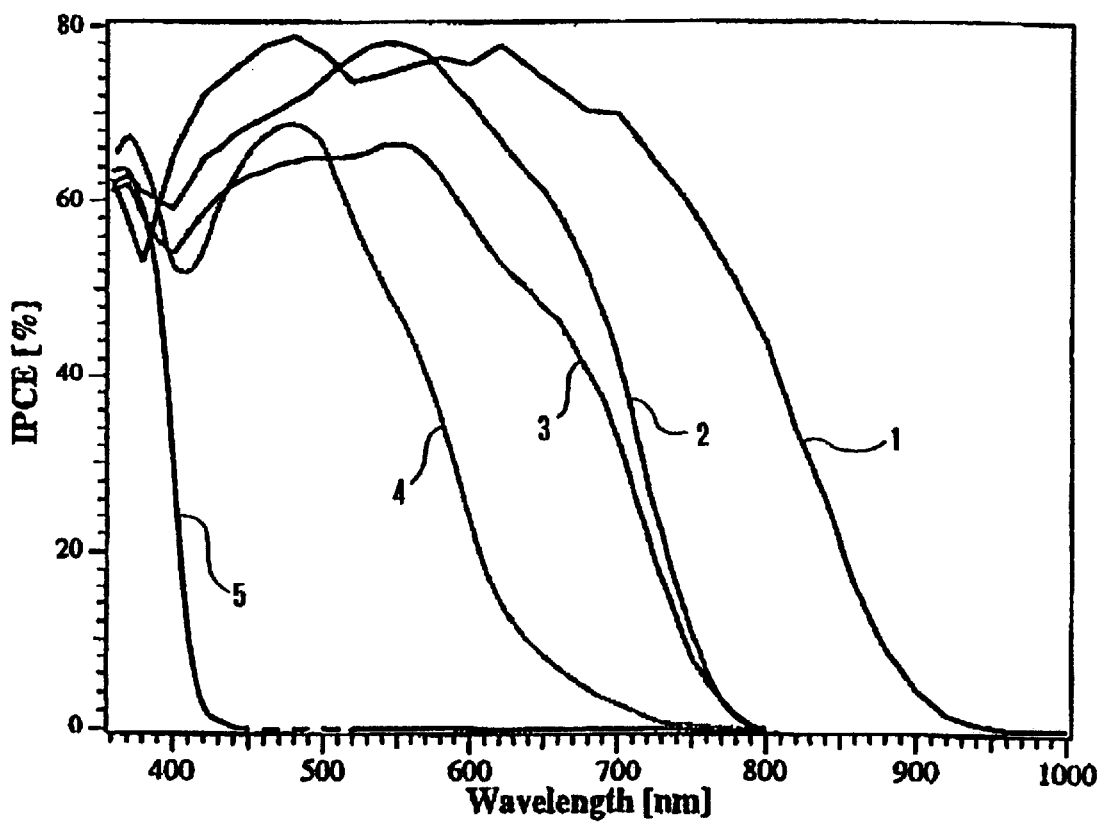
FIG. 3 is a graph, similar to the graph of FIG. 2, showing the respective photocurrent action spectra of a photovoltaic cell using the transition metal complex of formulae (Ia) or (Ib), in comparison with a similar cell using the cis-dithiocyanato-bis(4,4'-dicarboxy-2,2'-bipyridine) ruthenium (II) complex, of the prior art, as well as with two other similar cells using respectively two other prior art ruthenium complexes as a charge transfer photosensitizer for a semiconductive titanium dioxide photoanode layer, and with still another similar photovoltaic cell using no photosensitizer.

The comparison of the curves, shown in FIG. 3, illustrating, respectively:

Curve 1: the photocurrent action spectrum of the above-described photovoltaic cell using the transition metal complex of formula (I) as a charge transfer photosensitizer;

Curve 2: the photocurrent action spectrum of a similar photovoltaic cell using the prior art photosensitizer cis-dithiocyanatobis(4,4'-dicarboxy-2,2'-bipyridine) ruthenium(II) complex;

Curve 3: the photocurrent action spectrum of another similar photovoltaic cell using a prior art photosensitizer having the formula, RuL$_2$[Ru(bpy)$_2$(CN)$_2$]$_2$, where bpy means bipyridyl, and L is 4,4'-dicarboxy-2,2'-bipyridine;

Curve 4: the photocurrent action spectrum of still another similar photovoltaic cell using a prior art photosensitizer having the formula RuL$_3$, where L has the above-indicated meaning; and Curve 5: the photocurrent action spectrum of still another similar photovoltaic cell using no photosensitizer.

clearly demonstrates the superiority of the complex of formula (I), with regard to the spectral response in the read and near infrared regions, as well as the overall efficiency of panchromatic sensitization over the whole visible radiation spectrum.

What is claimed is:

1. A photosensitizer complex of formula (Ia)

$$MX_3L_t \qquad (Ia)$$

in which

M is a transition metal selected from ruthenium, osmium, iron, rhenium and technetium;

each X is a co-ligand independently selected from NCS$^-$, Cl$^-$, Br$^-$, I$^-$, CN$^-$, NCO$^-$, H$_2$O, NCH$^{2-}$ and pyridine unsubstituted or substituted by at least one group selected from vinyl, primary, secondary or tertiary amine, OH and C$_{1-30}$ alkyl; and L$_t$ is a tridentate ligand having a formula selected from the general formulae (IIa) and (IIb):

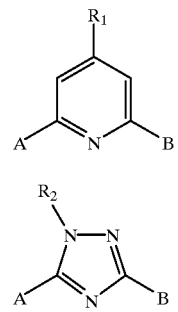

IIa

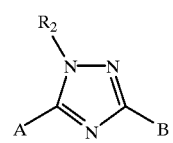

IIb wherein

R$_1$ is selected from H, COOH, PO(OH)$_2$, PO(OR$_3$)(OH), CO(NHOH), pyrocatechol group and phenyl substituted by at least one of the groups selected from COOH, PO(OH)$_2$, PO(OR$_3$)(OH) and CO(NHOH); R$_3$ being selected from C$_{1-30}$ alkyl and phenyl; R$_2$ is selected from H, C$_{1-30}$ alkyl and phenyl; and A and B are same or different groups independently selected from the groups of formulae (IIIa), (IIIb), (IIIc), (IIId), (IIIe) and (IIIf):

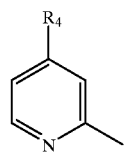

IIIa

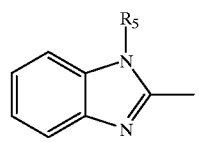

IIIb

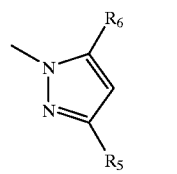

IIIc

-continued

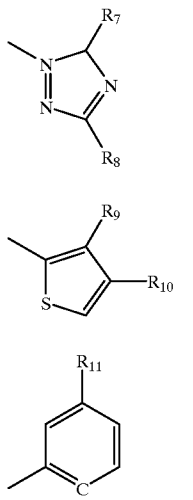

wherein

R$_4$ has the same meaning as R$_1$;

each R$_5$, R$_6$, R$_7$, R$_8$, R$_9$, R$_{10}$ and R$_{11}$ has the same meaning as R$_2$, the R$_2$, R$_5$, R$_6$, R$_7$, R$_8$, R$_9$, R$_{10}$ and R$_{11}$ being same as or different from each other;

with the proviso that at least one of the substituents R$_1$ and R$_4$ is different of H.

2. A photosensitizer complex of formula (Ia), according to claim 1, characterized in that M is ruthenium or osmium;

each X is independently selected from NCS$^-$ and CN$^-$; and

L$_t$ has the formula (IIa):

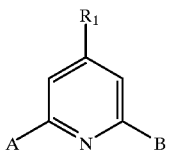

IIa wherein

R$_1$ is a phenyl substituted by at least one of the groups selected from COOH, PO(OH)$_2$, PO(OR$_3$)(OH) and CO(NHOH); R$_3$ being selected from C$_{1-30}$ alkyl and phenyl; and A and B are both 2-pyridyl.

3. A photosensitizer complex of formula (Ia), according to claim 1, characterized in that M is ruthenium or osmium;

each X is independently selected from NCS$^-$ and CN$^-$; and

L$_t$ has the formula (IIa):

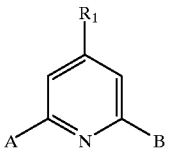

IIa wherein

R$_1$ is a COOH; and

A and B are both 4-carboxy-2-pyridyl.

4. A photosensitizer complex of formula (Ib)

$$MX_3L_t \quad (Ib)$$

in which

M is ruthenium;

each X is a co-ligand independently selected from NCS$^-$, Cl$^-$, Br$^-$, I$^-$, CN$^-$, NCO$^-$, H$_2$O, NCH$^{2-}$ and pyridine unsubstituted or substituted by at least one group selected from vinyl, primary, secondary or tertiary amine, OH and C$_{1-30}$ alkyl;

Y is a co-ligand selected from o-phenanthroline and 2,2'-bipyridine, unsubstituted or substituted by at least one C$_{1-30}$ alkyl; and L$_t$ is a tridentate ligand having a formula selected from the general formulae (IIa) and (IIb):

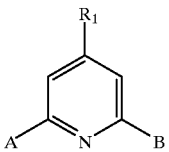

IIa

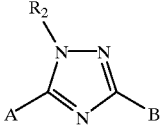

IIb wherein

R$_1$ is selected from H, COOH, PO(OH)$_2$, PO(OR$_3$)(OH), CO(NHOH), pyrocatechol group, and phenyl substituted by at least one of the groups selected from COOH, PO(OH)$_2$, PO(OR$_3$)(OH) and CO(NHOH);

R$_3$ being selected from C$_{1-30}$ alkyl and phenyl;

R$_2$ is selected from H, C$_{1-30}$ alkyl and phenyl; and

A and B are same or different groups independently selected from the groups of formulae (IIIa), (IIIb), (IIIc), (IIId), (IIIe) and (IIIf):

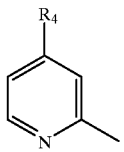

IIIa

-continued

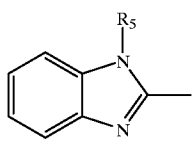

IIIb

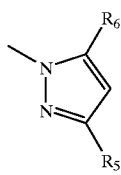

IIIc

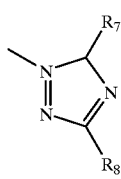

IIId

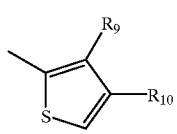

IIIe

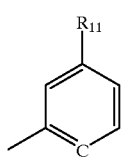

IIIf wherein
  $R_4$ has the same meaning as $R_1$;
  each $R_5$, $R_6$, $R_7$, $R_8$, $R_9$, $R_{10}$ and $R_{11}$ has the same meaning as $R_2$, the $R_2$, $R_5$, $R_6$, $R_7$, $R_8$, $R_9$, $R_{10}$ and $R_{11}$ being same as or different from each other;
  with the proviso that at least one of the substituents $R_4$ is different of H.

5. A photosensitizer complex of formula (Ib), according to claim 4, characterized in that
  each X is independently selected from NCS⁻ and CN⁻; and
  $L_t$ has the formula (IIa):

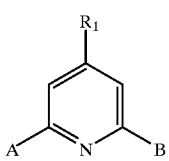

IIa wherein
  $R_1$ is a COOH; and
  A and B are both 4-carboxy-2-pyridyl.

6. A photosensitizer complex of formula (Ib)

MXYL$_t$ (Ib)

in which
  M is ruthenium;

each X is a co-ligand independently selected from NCS⁻, Cl⁻, Br⁻, I⁻, CN⁻, NCO⁻, H$_2$O, NCH$^{2-}$ and pyridine unsubstituted or substituted by at least one group selected from vinyl, primary, secondary or tertiary amine, OH and C$_{1-30}$ alkyl; and Y is a co-ligand selected from o-phenanthroline and 2,2'-bipyridine, unsubstituted or substituted by at least one C$_{1-30}$ alkyl; and $L_t$ is a tridentate ligand having a formula selected from the general formula (IIa):

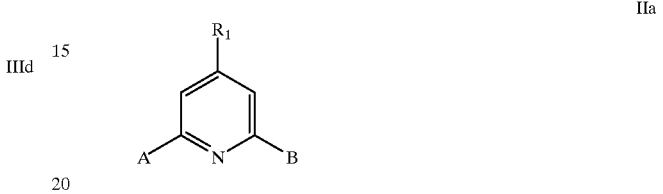

IIa wherein $R_1$ is selected from COOH, CO(NHOH), pyrocatechol group and phenyl substituted by at least one of the groups selected from COOH and CO(NHOH); and A and B are same or different groups independently selected from the groups of formulae (IIIa), (IIIb), (IIIc), (IIId), (IIIe) and (IIIf):

IIIa

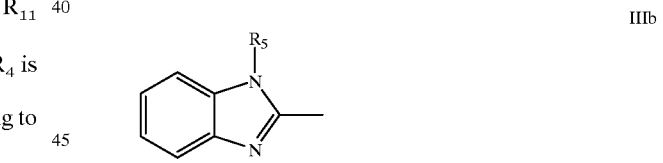

IIIb

IIIc

IIId

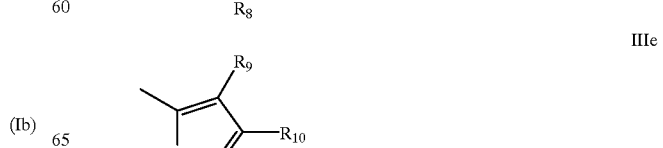

IIIe

-continued

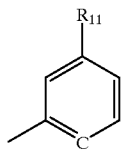
IIIf wherein

R$_4$ is H;

each R$_5$, R$_6$, R$_7$, R$_8$, R$_9$, R$_{10}$ and R$_{11}$ has the same meaning as R$_2$, is selected from H, C$_{1-30}$ alkyl and phenyl;

R$_5$, R$_6$, R$_7$, R$_8$, R$_9$, R$_{10}$ and R$_{11}$ being same as or different from each other.

7. A photosensitizer complex of formula (Ib), according to claim 6, characterized in that each X is independently selected from NCS$^-$ and CN$^-$; and L$_t$ has the formula (IIa):

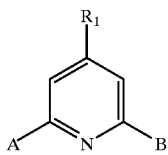
IIa wherein

R$_1$ is a phenyl substituted by at least one of the groups selected from COOH and CO(NHOH); and A and B are both 2-pyridyl.

8. A photosensitizer complex of formula (Ib)

MXYL$_t$ (Ib)

in which

M is a transition metal selected from osmium, iron, rhenium and technetium;

each X is a co-ligand independently selected from NCS$^-$, Cl$^-$, Br$^-$, I$^-$, CN$^-$, NCO$^-$, H$_2$O, NCN$^{2-}$ and pyridine unsubstituted or substituted by at least one group selected from vinyl, primary, secondary or tertiary amine, OH and C$_{1-30}$ alkyl;

Y is a co-ligand selected from o-phenanthroline and 2,2'-bipyridine, unsubstituted or substituted by at least one C$_{1-30}$ alkyl; and L$_t$ is a tridentate ligand having a formula selected from the general formula (IIa) and (IIb):

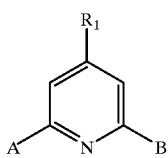
IIa

-continued

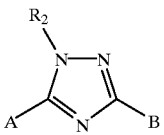
IIb wherein

R$_1$ is selected from H, COOH, PO(OH)$_2$, PO(OR$_3$)(OH), CO(NHOH), pyrocatechol group, and phenyl substituted by at least one of the groups selected from COOH, PO(OH)$_2$, PO(OR)$_3$(OH) and CO(NHOH);

R$_3$ being selected from C$_{1-30}$ alkyl and phenyl;

R$_2$ is selected from H, C$_{1-30}$ alkyl and phenyl; and

A and B are same or different groups independently selected from the groups of formulae (IIIa), (IIIb), (IIIc), (IIId), (IIIe) and (IIIf):

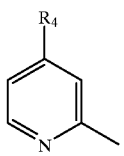
IIIa

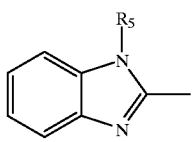
IIIb

IIIc

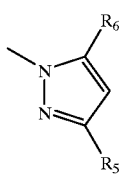
IIId

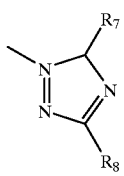
IIIe

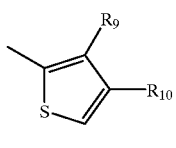

IIIf

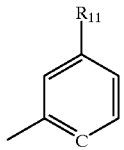

wherein $R_4$ is the same meaning as $R_1$;

each $R_5$, $R_6$, $R_7$, $R_8$, $R_9$, $R_{10}$ and $R_{11}$ has the same meaning as $R_2$, the $R_2$, $R_5$, $R_6$, $R_7$, $R_8$, $R_9$, $R_{10}$ and $R_{11}$ being same as or different from each other;

with the proviso that at least one of the substituents $R_1$ and $R_4$ is different of H.

9. A photosensitizer complex of formula (Ia), according to claim 1, characterized in that M is osmium;

each X is independently selected from $NCS^-$ and $CN^-$; and $L_t$ has the formula (IIa):

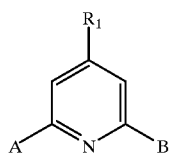

IIa wherein $R_1$ is a phenyl substituted by at least one of the groups selected from COOH, $PO(OH)_2$, $PO(OR_3)(OH)$ and CO(NHOH); $R_3$ being selected from $C_{1-30}$ alkyl and phenyl; and A and B are both 2-pyridyl.

10. A photosensitizer complex of formula (Ib), according to claim 8, characterized in that M is osmium;

each X is independently selected from $NCS^-$ and $CN^-$; and $L_t$ has the formula (IIa):

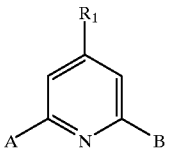

IIa wherein $R_1$ is COOH; and

A and B are both 4-carboxy-2-pyridyl.

11. A photovoltaic cell comprising an electrically conductive layer deposited on a support to which at least one titanium dioxide layer has been applied, characterised in that it comprises, as a photosensitizer applied to the titanium dioxide layer, a photosensitizer complex of formula (Ia) as specified in claim 1.

12. A photovoltaic cell comprising an electrically conductive layer deposited on a support to which at least one titanium dioxide layer has been applied, characterised in that it comprises, as a photosensitizer applied to the titanium dioxide layer, a photosensitizer complex of formula (Ib) as specified in claim 4.

13. A photovoltaic cell comprising an electrically conductive layer deposited on a support to which at least one titanium dioxide layer has been applied, characterised in that it comprises, as a photosensitizer applied to the titanium dioxide layer, a photosensitizer complex of formula (Ib) as specified in claim 6.

14. A photovoltaic cell comprising an electrically conductive layer deposited on a support to which at least one titanium dioxide layer has been applied, characterised in that it comprises, as a photosensitizer applied to the titanium dioxide layer, a photosensitizer complex of formula (Ib) as specified in claim 8.

* * * * *

UNITED STATES PATENT AND TRADEMARK OFFICE
CERTIFICATE OF CORRECTION

PATENT NO. : 6,245,988 B1
DATED : June 12, 2001
INVENTOR(S) : Michael Gratzel, Mohammad Khaja Nazeeruddin, Peter Pechy It is certified that error appears in the above-identified patent and that said Letters Patent is hereby corrected as shown below:

Title page,
Item [30], Foreign Application Priority Data, please delete "Jul. 5, 1997" and insert in lieu thereof -- May 7, 1997 --.
Item [57], ABSTRACT,
Lines 5 and 6, please delete "NCS--, Cl--, Br--, I--, CN--, NCO--" and insert in lieu thereof -- $NCS^-$, $Cl^-$, $Br^-$, $I^-$, $CN^-$, $NCO^-$ --.
Line 16, please delete "formula (1a) or 1b)" and insert in lieu thereof -- formula (1a) or (1b) --.

Column 3,
Line 23, please delete "More perferably" and insert in lieu thereof -- Preferably --.

Column 4,
Line 42, please delete "formula (11b)" and insert in lieu thereof -- formula (1b) --.

Column 5,
Line 16, please delete "being selected from $C_{1-30}$ alkyl and phenyl" and insert in lieu thereof -- being seleted from H, $C_{1-30}$ alkyl and phenyl --.
Line 25, insert -- X is $NCS^-$ or $CN^-$ -- at the end.

Column 8,
Line 60, please delete "8.40 (2H, s), 8.55 (2H, d)".

Column 9,
Line 33, please delete "(d, 2H, H-6, H-6")" and insert in lieu thereof -- (d, 2H, H-6, H-6') --.
Line 47, please delete "Syntheses, 1961, 56)" and insert in lieu thereof -- Synthesis, 1981, 56) --.
Line 66, please delete "terpyridyl)" and insert in lieu thereof -- terpyridine --.

Column 10,
Line 27, please delete "$RU(NC)_3L_t$" and insert in lieu thereof -- $Ru(NC)_3L_t$ --.

Column 11,
Line 6, please delete "110°C. For a further 4 hours" and insert in lieu thereof -- 110°C for a further 4 hours --.

Column 12,
Line 63, please delete "band at 400 nm" and insert in lieu thereof -- band at 490 nm --.

UNITED STATES PATENT AND TRADEMARK OFFICE
CERTIFICATE OF CORRECTION

PATENT NO.    : 6,245,988 B1
DATED         : June 12, 2001
INVENTOR(S)   : Michael Gratzel, Mohammad Khaja Nazeeruddin, Peter Pechy It is certified that error appears in the above-identified patent and that said Letters Patent is hereby corrected as shown below:

Column 13,
Line 2, please delete "Os(NC)Yl$_t$" and insert in lieu thereof -- Os(NC)YL$_t$ --.
Lines 20 and 28, please delete "colloid" and insert in lieu thereof -- colloidal --.

Column 14,
Line 18, please delete "TCl$_4$" and insert in lieu thereof -- TiCl$_4$ --.

Column 16,
Line 13, please delete "NCH$^{2-}$" and insert in lieu thereof -- NCN$^{2-}$ --.

Column 18,
Line 18, please delete "MX$_3$L$_t$" and insert in lieu thereof -- MXL$_t$ --.
Line 23, please delete "NCH$^{2-}$" and insert in lieu thereof -- NCN$^{2-}$ --.

Column 20,
Line 2, please delete "NCH$^{2-}$" and insert in lieu thereof -- NCN$^{2-}$ --.

Column 21,
Lines 13 and 14, please delete "has the same meaning as R$^2$".

Column 23,
Line 8, please delete "formula (1a)" and insert in lieu thereof -- formula (1b) --.
Lines 8 and 9, please delete "according to claim 1" and insert in lieu thereof -- according to claim 8 --.

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,245,988 B1
DATED : June 12, 2001
INVENTOR(S) : Michael Graetzel, Mohammad Khaja Nazeeruddin and Peter Pechy It is certified that error appears in the above-identified patent and that said Letters Patent is hereby corrected as shown below:

Title page,
Item [75], Inventors, please delete "Michael Grätzel" and insert in lieu thereof
-- Michael Graetzel --.
Item [57], ABSTRACT,
Line 16, please delete "formula (Ia) or Ib)" and insert in lieu thereof -- formula (Ia) or (Ib) --. (Roman numerals instead of Arabic numerals)

Column 4,
Line 42, please delete "formula (IIb)" and insert in lieu thereof -- formula (Ib) --. (Roman numerals instead of Arabic numerals)

Column 13,
Line 2, please delete "$Os(NC)Yl_t$" and insert in lieu thereof -- $Os(NCS)Ylt$ --.

Column 18,
Line 18, please delete "$MX_3L_t$" and insert in lieu thereof -- $MXYL_t$ --.

Column 21,
Lines 13 and 14, please delete "has the same meaning as $R_2$".

Column 23,
Line 8, please delete "formula (Ia)" and insert in lieu thereof -- formula (Ib) --. (Roman numerals instead of Arabic numerals)

Signed and Sealed this

Nineteenth Day of April, 2005

JON W. DUDAS
*Director of the United States Patent and Trademark Office*